United States Patent [19]

Shealy et al.

[11] Patent Number: 4,730,001

[45] Date of Patent: Mar. 8, 1988

[54] CARBOCYCLIC ANALOGUES OF AMINO AND AZIDO THYMIDINES

[75] Inventors: Y. Fulmer Shealy; C. Allen O'Dell, both of Birmingham, Ala.

[73] Assignee: Southern Research Institute, Birmingham, Ala.

[21] Appl. No.: 820,790

[22] Filed: Jan. 22, 1986

[51] Int. Cl.$^4$ ............... C07D 239/26; A61K 31/505
[52] U.S. Cl. ................... 514/274; 544/312
[58] Field of Search ............... 544/312, 311, 314, 274

[56] References Cited

U.S. PATENT DOCUMENTS 4,396,623  8/1983  Shealy ................... 544/309

OTHER PUBLICATIONS

Chemical Abstracts, vol. 104 (1986), p. 733, Entry Nos. 130206y and 130207z.
Shealy and Clayton, *Journal of the American Chemical Society*, vol. 88, pp. 3885–3887, 1966.
C. Desgranges et al, *Biochemical Pharmacology*, vol. 32, pp. 3583–3590, 1983, Horwitz et al, *J. Org. Chem.*, pp. 3045–3048, 1962.
Neenan et al, *J. Med. Chem.*, pp. 580–581, 1973.
Cheng et al, *Biochemistry*, pp. 1179–1185, 1974.
Cheng et al., *Biochemistry*, pp. 2612–2619, 1973.
Chen et al, *Antimicrob. Agents Chemother.*, pp. 433–436, 1980.
Letsinger et al, *J. Am. Chem. Soc.*, pp. 292–293, 1972.
Lin et al, *J. Med. Chem.*, pp. 495–498, 1976.
Lin et al, *J. Med. Chem.*, pp. 109–112, 1978.
Miller et al, *J. Org. Chem.*, pp. 1772–1776, 1964.
Horwitz et al, *J. Org. Chem.*, pp. 2076–2078, 1964.
Matsuda et al, *J. Org. Chem.*, pp. 3274–3278, 1980.
Lin et al, *Biochem. Pharmacol.*, pp. 125–128, 1982.
Chen et al, *Molecular Pharmacol.*, pp. 441–445, 1984.
Shealy et al, *Journal of Heterocyclic Chemistry*, vol. 20, pp. 655–661, 1983.
Shannon et al, *Antimocrob. Agents Chemother.*, pp. 769–776, 1981.

*Primary Examiner*—Donald G. Daus
*Assistant Examiner*—Barbara Cassatt
*Attorney, Agent, or Firm*—Roylance, Abrams, Berdo & Goodman

[57] ABSTRACT

There are disclosed compounds represented by Formulas I–III:

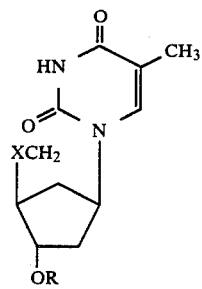

Formula I

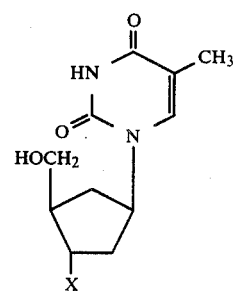

Formula II

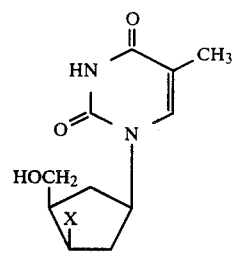

Formula III wherein X is an azido group or an amino group and R is hydrogen or an acyl group. These compounds are useful for the treatment of viral infections and/or as intermediates in the production of compounds which are useful in the treatment of viral infections.

14 Claims, No Drawings

CARBOCYCLIC ANALOGUES OF AMINO AND AZIDO THYMIDINES

BACKGROUND OF THE INVENTION

This invention relates to carbocyclic analogues of amino and azido thymidines and to the use of such compounds in the treatment of viral infections.

The term "carbocyclic analogue of a nucleoside" designates a compound that has the same chemical structure as the nucleoside except that the oxygen atom of the furanose moiety of the nucleoside is replaced by a methylene group in the carbocyclic analogue; or, differently expressed, in the carbocyclic analogue a cyclopentane ring replaces the tetrahydrofuran ring of the analogous nucleoside. Such nucleoside analogues were designated carbocyclic analogues of nucleosides by Shealy and Clayton, *Journal of the American Chemical Society*, Volume 88, pages 3885-3887, 1966. The natural nucleosides and many of their true nucleoside analogues are subject to the action of enzymes (phosphorylases and hydrolases) that cleave the nucleosides to the pentose and purine or pyrimidine moieties. For example, it has been reported by C. Desgranges et al. (*Biochemical Pharmacology*, Vol. 32, pages 3583-3590, 1983) that various 5-substituted-2'-deoxyuridines including 5-ethyl-2'-deoxyuridine (EDU) and 5-[(E)-2-(bromovinyl)]-2'-deoxyuridine (BVDU) are substrates for thymidine phosphorylase isolated from human blood platelets. The biological effects of such true nucleoside analogues may be lessened by the action of these degradative enzymes. In contrast, carbocyclic analogues of nucleosides do not possess the glycosidic bond present in the true nucleosides and, therefore, are not subject to the action of these degradative enzymes. They may also be more selective in their biological actions.

5'-Amino-5'-deoxythymidine (Chart I, Compound 1, 5'-amino-5'-dThd) and the 5'-azido derivative (Compound 2) were synthesized initially by Horwitz et al (*J. Org. Chem.*, 1962, 27, 3045-3048). Subsequent studies have shown that 5'-amino-5'-dThd is a good inhibitor of thymidine kinase from tumor cells (Neenan et al, *J. Med. Chem.*, 1973, 16, 580-581 and Cheng et al, *Biochemistry*, 1974, 13, 1179-1185) and a weak inhibitor of thymidylate kinase (Cheng et al, *Biochemistry*, 1973, 12, 2612-2619); that it is phosphorylated to the 5'-N-diphosphate in cells infected with type 1 herpes simplex virus (HSV-1), but not by a mixture of thymidine kinase and thymidylate kinase from uninfected mammalian cells (Chen et al, *Antimicrob. Agents Chemother.*, 1980, 18, 433-436); and that its 5'-N-triphosphate is incorporated into DNA (Letsinger et al, *J. Am. Chem. Soc.*, 1972, 94, 292-293). 5'-Amino-5'-dThd is a selective inhibitor of HSV-1 replication in cultured cells, but it is not an effective inhibitor of mouse neoplastic cells (L1210 leukemia and Sarcoma 180) (Lin et al, *J. Med. Chem.*, 1976, 19, 495-498 and Lin et al, *J. Med. Chem.*, 1978, 21, 109-112). In contrast, 3'-amino-3'-deoxythymidine (Miller et al, *J. Org. Chem.*, 1964, 29, 1772-1776 and Horwitz et al, *J. Org. Chem.*, 1964, 29, 2076-2078) (Chart I, Compound 3, 3'-amino-3'-dThd) has only slight antiviral activity (Lin et al, *J. Med. Chem.*, 1978, 21, 109-112), but it has potent activity against L1210 leukemia (Lin et al, *J. Med. Chem.*, 1978, 21, 109-112), sarcoma 180 (Lin et al, *J. Med. Chem.*, 1978, 21, 109-112), and P815 mouse leukemia (Matsuda et al, *J. Org. Chem.*, 1980, 45, 3274-3278) cells in culture ($ED_{50}=1$ μM, 5 μM, 0.08 mcg/mL, respectively). In tests against L1210 leukemia in vivo, Lin et al (*Biochem. Pharmacol.*, 1982, 31, 125-128) showed that 3'-amino-3'-dThd can increase markedly the survival times of treated mice, and Chen et al (*Molecular Pharmacol.*, 1984, 25, 441-445) also presented evidence that inhibition of the DNA polymerase reaction is a major site of the inhibitory effects of 3'-amino-3'-dThd.

Following is Chart I:

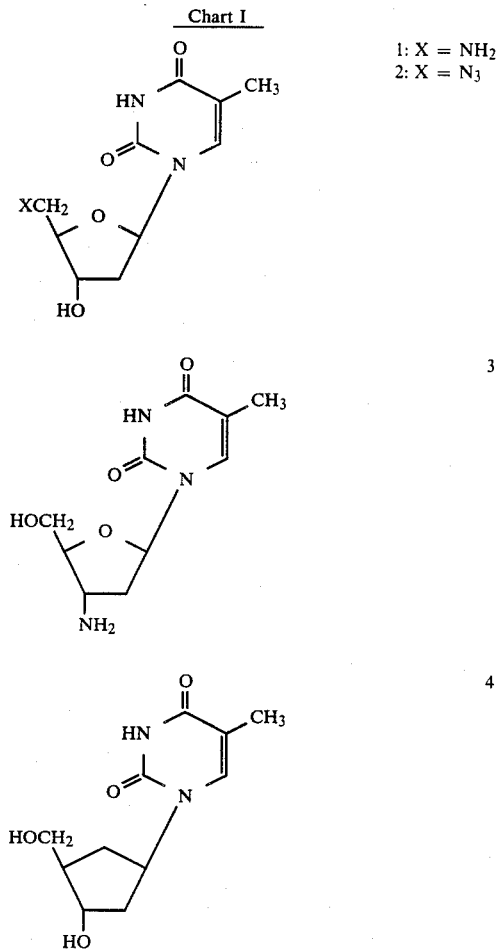

Chart I

1: X = NH$_2$
2: X = N$_3$

SUMMARY OF THE INVENTION

The compounds of this invention are represented by Formulas I-III:

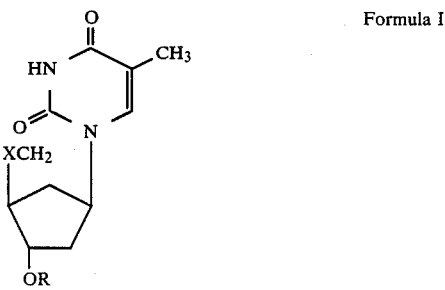

Formula I

Formula II

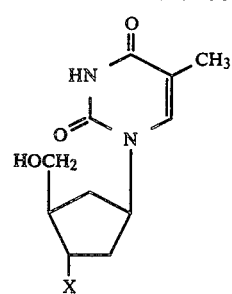

Formula III

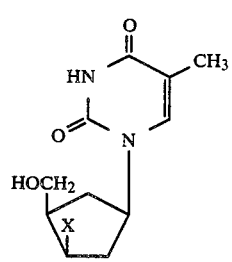

wherein X is an azido group or an amino group and R is hydrogen or an acyl group, preferably one having from 2–7 carbon atoms such as an acetyl group. Compounds of this invention are useful for the treatment of viral infections by administering a therapeutically effective amount of same to a host animal, including man, and/or as intermediates in the production of compounds which are useful for the treatment of viral infections.

DETAILED DESCRIPTION OF THE INVENTION

The trivial name of a carbocyclic (cyclopentyl) analogue of a nucleoside is formed by prefixing C- to the trivial name of the corresponding nucleoside.

The carbocyclic analogues of the amino and azido thymidines of this invention are synthesized by beginning with certain derivatives of the carbocyclic analogue of thymidine (Chart I, Compound 4). Syntheses of these carbocyclic thymidine derivatives (Compounds 5, 9, and 13 of Charts II–IV) are described by Shealy et al in *Journal of Heterocyclic Chemistry*, Vol. 20, pages 655–661 (1983), the disclosure of which is incorporated herein by reference.

The synthesis route to C-5'-amino-5'-dThd is outlined in Chart II. The synthesis of the carbocyclic analogue of 3'-amino-3'-dThd is summarized in Chart III and the synthesis of the corresponding all-cis isomer of that compound is outlined in Chart IV. In Chart II, "Ac" stands for acetyl; and in Charts III and IV, "Tr" stands for triphenylmethoxy. Charts II, III and IV are as follows:

Chart II

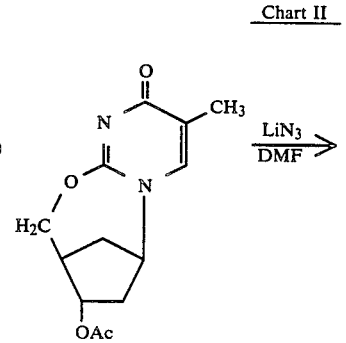

5

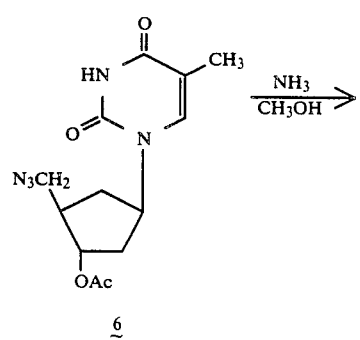

6

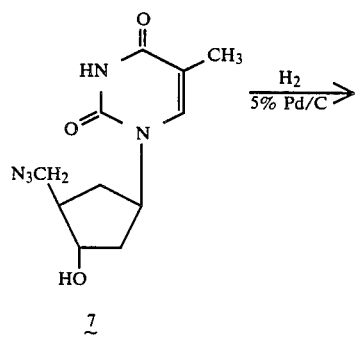

7

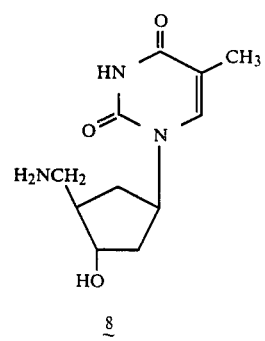

8

Chart III

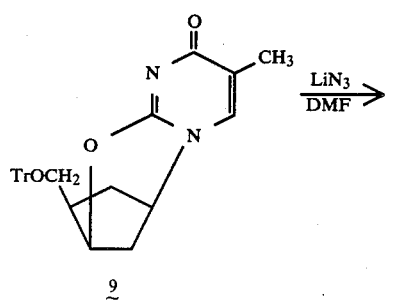
9

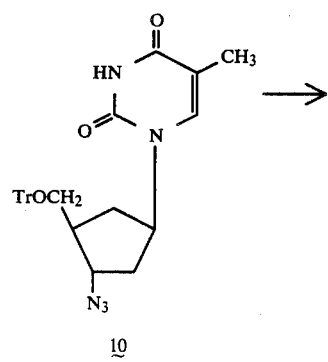
10

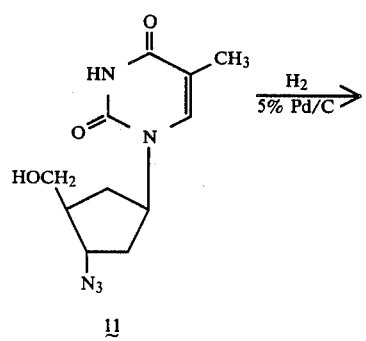
11

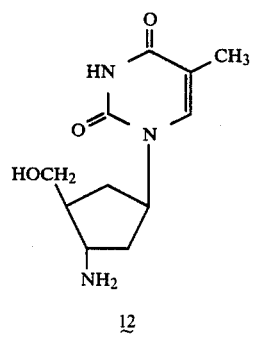
12

Chart IV

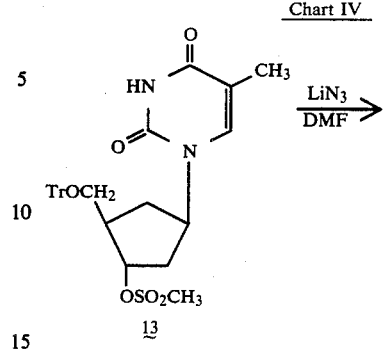
13

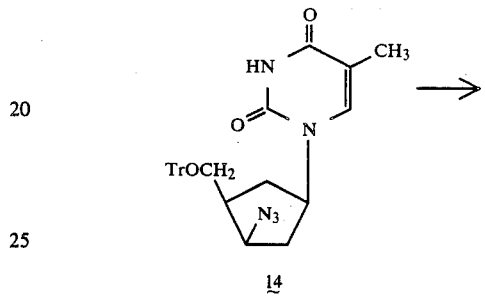
14

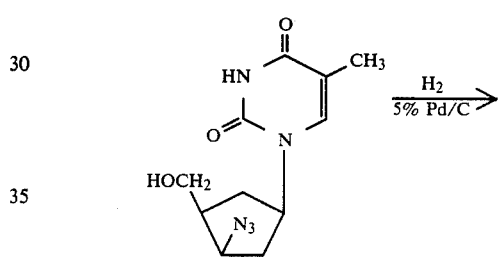
15

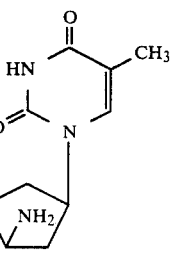
16

Compounds prepared in accordance with this invention are illustrated by, but are not limited to, the following examples. In these examples, decomposition and melting temperatures (mp) were determined in capillary tubes heated in a Mel-Temp apparatus. Ultraviolet spectra (UV) were recorded with a Cary Model 17 spectrophotometer and absorption maxima are reported in nanometers; solutions for ultraviolet spectral determinations were prepared by diluting a 5-mL aliquot of a water or ethanol solution to 50 mL with 0.1N hydrochloric acid, phosphate buffer (pH 7), or 0.1N sodium hydroxide. Absorption maxima of these solutions are reported as being determined at pH 1, 7 or 13, respectively. Infrared spectra (IR) were recorded with a Nicolet MX-IE spectrometer from samples in potassium bromide disks; vs=very strong, s=strong, sh=shoulder. Mass spectral data (MS) were taken from low-resolution, electron-impact spectra determined at 70 eV unless indicated otherwise. The peaks listed are those arising from the molecular ion (M), those attributable to the loss of certain fragments (M minus a fragment), and some other prominent peaks. Fragments containing the complete thymine moiety may be designated Thy plus an atom or group. Proton NMR spectra (Table 2) were determined at 300.64 MHz with a Nicolet 300 NB NMR spectrometer. The solvent was DMSO-$D_6$ and the internal standard was tetramethylsilane; s=singlet, m=multiplet, t=triplet. Thin-layer chromatography (TLC) was performed on plates of silica gel and developed plates were examined by UV light (254 nm). The ultraviolet absorption data and the nuclear magnetic resonance data for Examples 1 to 8 are set forth in Tables 1 and 2, respectively.

In the Examples, the various compound numbers refer to the compounds shown in Charts II, III and IV. These compounds are named in accordance with current usage of the *Chemical Substance Index of Chemical Abstracts*.

EXAMPLE 1

(+)-1-[(1α,3β,4α)-4-(Azidomethyl)-3-hydroxycyclopentyl]-5-methyl-2,4(1H,3H)-pyrimidinedione
(Compound 7)

A solution of 200 mg (0.76 mmol) of Compound 5 obtained by the procedure described by Shealy et al, *Journal of Heterocyclic Chemistry*, Vol, 20, pages 655–661 (1983), and 121 mg (2.46 mmol) of lithium azide in 10 mL of dry dimethylformamide was heated at 100° C. in an atmosphere of dry nitrogen for seven hours. Volatile components were evaporated from the reaction mixture under reduced pressure, and the gummy residue was dissolved in methanol. The solution was applied to a preparative silica gel TLC plate, the plate was developed in 9:1 chloroform:methanol, and the product band was removed and extracted in a Soxhlet extractor with ethanol. The filtered extract was concentrated in vacuo to an orange, glassy residue: weight of Compound 6, 148 mg (64%); MS (direct-probe temperature, 230° C.) m/e 307 (M), 279 (307-CO), 265 (307-$N_3$), 236 (M—CO—Ac), 220 (M—CO—OAc), 193, 192, 177, 153 (Thy+$C_2H_4$), 148, 147, 127 (Thy+2H), 126 (Thy+H); IR (strong and medium-strong bands, 2200-600 cm$^{-1}$ region) 2100, 1735 sh, 1690 vs, 1470, 1450, 1370, 1270 sh, 1245.

A solution of 145 mg (0.47 mmol) of Compound 6 in 5 mL of ammonia-methanol (15% ammonia) was stirred at room temperature for 25 hours and then concentrated to dryness under reduced pressure. The crude product was chromatographed in 95:5 chloroform:methanol (application and elution solvent) on a column of silica gel. Concentration of product-containing fractions (determined by TLC) afforded 104 mg (83%) of a colorless syrup. Attempts to crystallize this material from various solvents failed and it was evaporated with several portions of ethanol: weight of Compound 7, 95 mg; TLC, 1 spot (60 mcg, 9:1 chloroform:methanol); IR (strong and medium-strong bands, 2200-600 cm$^{-1}$ region) 2100 s, 1690 vs, 1475, 1275. Anal. Calculated for $C_{11}H_{15}N_5O_3 \cdot \frac{1}{8}C_2H_5OH$: C, 49.85; H, 5.86; N, 25.84. Found: C, 50.21; H, 5.83; N, 25.91.

EXAMPLE 2

(+)-1-[(1α,3β,4α)-4-(Aminomethyl)-3-hydroxycyclopentyl]-5-methyl-2,4(1H,3H)-pyrimidinedione
(Compound 8)

A solution of 82 mg (0.31 mmol) of Compound 7 in 10 mL of methanol that contained 25 mg of 5% palladium-on-charcoal was hydrogenated at atmospheric pressure and room temperature for 20 hours. Hydrogen uptake could not be measured because reduction of the azide group resulted in evolution of nitrogen in the closed system. The catalyst was separated by filtration, and the combined filtrate and methanol washings were concentrated in vacuo to a syrupy residue that crystallized upon chilling. The residue was triturated with ethyl acetate, collected by filtration, washed with ethyl acetate and dried in vacuo: yield of Compound 8, 42 mg (57% yield); mp, darkens above 170° C., 186°–189° C. dec (inserted at 100° C., 3° C./min); TLC, 1 spot (40 or 80 mcg applied, ethanol-conc. ammonium hydroxide (4:1) as developing solvent); UVmax 211 (ε8700), 273 (ε10,000) at pH 1; 209 (ε9000), 273 (ε10,400) at pH 7; 272 (ε8100) at pH 13; MS (direct-probe temperature, 140° C.) m/e 239 (M), 222 (M—OH), 221 (M—$H_2O$), 210 (M—$CH_2NH_2$+H), 193 (M—OH—$CH_2NH_2$+H), 153 (Thy+$C_2H_4$), 127 (Thy+2H), 126 (Thy+H); IR (strong and medium-strong bands, 1800-600 cm$^{-1}$ region) 1695 sh, 1665 s, 1615, 1500, 1475, 1465 sh, 1355, 1295, 1075, 1055, 910, 790. Anal. Calculated for $C_{11}H_{17}N_3O_3 \cdot \frac{1}{2}CH_3OH$: C, 54.10; H, 7.50; N, 16.46. Found: C, 54.36; H, 7.44; N, 16.23.

EXAMPLE 3

(+)-1-[(1α,3β,4α)-3-Azido-4-[(triphenylmethoxy)methyl]cyclopentyl]-5-methyl-2,4(1H,3H)pyrimidinedione
(Compound 10)

A solution of 1.40 g (3.01 mmol) of Compound 9 obtained by the procedure described by Shealy et al, supra, and 480 mg (9.80 mmol) of lithium azide in 72 ml of dry dimethylformamide was heated at 100° C. under an atmosphere of nitrogen for 72 hours. An additional 480 mg (9.80 mmol) of lithium azide was added, and heating was continued for seven days. Thin layer chromatography indicated that reaction was complete, and the reaction mixture was cooled and filtered. The combined filtrate and dimethylformamide washings were evaporated in vacuo to dryness, and the residue was extracted with 50 mL of 98:2 chloroform:methanol. The mixture was filtered to remove inorganic material, and the combined filtrate and washings were concentrated to dryness in vacuo. The residue was triturated with ether (25 mL), and the white solid that separated was filtered away, washed thoroughly with ether, and dried in vacuo at 56° C.: yield, 1.47 g (96%); mp, 200°–205° C. dec (inserted at 180° C., 3°/min). Additional Compound 10 [55 mg (4%)] was obtained by concentrating the first-crop filtrate to dryness and triturating the residue with methanol. The crops were combined and recrystallized from 55 mL of boiling methanol; weight, 975 mg (64% recovery); mp, 205°–207° C. dec (inserted at 180° C., 3° C./min); TLC, 1 spot (20 or 40 mcg, 95:5 chloroform-methanol as developing solvent); MS (field desorption; 13 mA; solvent, DMSO) m/e 507 (M); IR (strong and medium-strong bands, 2200-600 cm$^{-1}$ region) 2105 s, 1685 vs, 1650 s, 1450, 1255, 710. Anal. Calculated for $C_{30}H_{29}N_5O_3$: C, 70.99; H, 5.76; N, 13.80. Found: C, 70.81; H, 6.02; N, 13.63.

A second crop (240 mg, 16% recovery) was obtained by concentrating the filtrate to about one-fourth of its original volume: mp, 203°–205° C. dec (inserted at 180° C., 3° C./min). Compound 10 can also be purified by chromatography on a column of silica gel with chloroform-methanol (98:2) as eluting solvent.

EXAMPLE 4

(+)-[(1α,3β,4α)-3-Azido-4-(hydroxymethyl)cyclopentyl]-5-methyl-2,4(1H,3H)-pyrimidinedione (Compound 11)

A solution of 1.21 g (2.38 mmol) of Compound 10 in 50 mL of 80% acetic acid was heated at reflux for ¼ hour. The solution was concentrated in vacuo to remove volatile components, and the residue was extracted with 25 mL of water. The insoluble portion (triphenylmethanol) was filtered away, and the combined filtrate and water washings were evaporated in vacuo; yield, 570 mg of a viscous residue. The crude product was chromatographed in 95:5 chloroform:methanol on a column of silica gel. Fractions of the eluate containing Compound 11 (determined by TLC) were combined and concentrated in vacuo to dryness. Trituration of the residue with ether afforded white crystals: yield, 472 mg (75%); mp, 154°–157° C. (inserted at 100° C., 3° C./min); TLC, 1 spot (40 or 80 mcg, 9:1 chloroform-methanol as developing solvent); UVmax 211 nm ($\epsilon$9700) and 273 $\epsilon$10,900) at pH 1, 210 ($\epsilon$10,000) and 273 ($\epsilon$11,000) at pH 7, 271 ($\epsilon$8400) at pH 13; MS (direct-probe temperature, 150° C.) m/e 265 (M), 237 (M—$N_2$), 219 (M—$N_2$—$H_2O$), 193, 178, 153 (Thy+$C_2H_4$), 127 (Thy+2H), 126 (Thy+H); IR (strong and medium-strong bands, 2200-600 $cm^{-1}$ region) 2115 s, 1685 s, 1670 s, 1645, 1300, 1275, 1055, 585. Anal. Calculated for $C_{11}H_{15}N_5O_3 \cdot \frac{1}{4}CH_3OH$: C, 49.44; H, 5.90; N, 25.63. Found: C, 49.66; H, 6.02; N, 25.81.

EXAMPLE 5

(+)-1-[(1α,3β,4α)-3-Amino-4-(hydroxymethyl)cyclopentyl]-5-methyl-2,4(1H,3H)-pyrimidinedione (Compound 12)

Compound 12 was prepared, by the procedure described for the preparation of Compound 8, by catalytic hydrogenation of Compound 11 (230 mg, 0.87 mmol) on 5% palladium-charcoal (60 mg) in methanol (20 mL). The residue that remained after concentration in vacuo crystallized when it was triturated with ethyl acetate. White, crystalline Compound 12 was collected by filtration, washed with ethyl acetate and dried in vacuo: yield, 178 mg (86%); mp, 188°–192° C. dec (inserted at 100° C., 3° C./min); TLC, 1 spot (40 and 80 mcg applied; 7:3 2-propanol-1M ammonium acetate as developing solvent); UVmax 272 ($\epsilon$10,000) at pH 1, 273 ($\epsilon$10,300) at pH 7, 271 ($\epsilon$8,000 at pH 13; MS (direct-probe temperature, 20° C.) m/e 239 (M), 196, 127 (Thy+2H), 126 (Thy+H); IR (strong and medium-strong bands, 1800-600 $cm^{-1}$ region) 1685 vs, 1470, 1455, 1445, 1385, 1365, 1280, 1265, 905, 760 sh, 755, 480, 410. Anal. Calculated for $C_{11}H_{17}N_3O_3 \cdot \frac{1}{4}H_2O$: C, 54.19; H, 7.23; N, 17.24. Found: C, 54.41; H, 7.59; N, 17.00.

EXAMPLE 6

(+)-1-[(1α,3α,4α)-3-Azido-4-[(triphenylmethoxy)methyl]cyclopentyl]-5-methyl-2,4(1H,3H)pyrimidinedione (Compound 14)

A solution of 2.42 g (4.32 mmol) of Compound 13 obtained by the procedure described by Shealy et al, supra, and 0.528 g (10.8 mmol) of lithium azide in 120 mL of dry dimethylformamide was heated at 100° C. for 20 hours. The reaction mixture was concentrated in vacuo to dryness and thoroughly dried at high vacuum. The residue was dissolved in 5 mL of 95:5 chloroform:methanol, filtered to remove inorganic material, and the filtrate was applied to a column containing 90 g of silica gel. The column was eluted with 95:5 chloroform:methanol, and product-containing fractions (determined by TLC) were combined and concentrated in vacuo to dryness. The residue crystallized when it was triturated with methanol, and Compound 14 was collected by filtration, washed with cold methanol, and dried in vacuo: yield, 982 mg (45%); mp, 210°–212° C. (inserted at 110° C., 3°/min); TLC, 1 spot (40 mcg applied, 95:5 chloroform-methanol); MS (direct-probe temperature, 250° C.) m/e 507 (M), 479 (M—$N_2$), 448, 447, 429, 401, 326, 264 (M—$CPh_3$), 260, 248 (M—$OCPh_3$), 243 ($CPh_3$), 183, 165, 127 (Thy+2H), 126 (Thy+H); IR (strong and medium-strong bands, 2200-800 $cm^{-1}$ region) 2105, 1695, 1680, 1645, 1470, 1445, 1270, 1065. Anal. Calculated for $C_{30}H_{29}N_5O_3$: C, 70.99; H, 5.76; N, 13.80. Found: 70.95; H, 5.94; N, 13.89. After standing, the filtrate deposited additional crystalline Compound 14: weight 228 mg (10%); mp, 206°–210° C. (inserted at 100° C., 3° C./min).

Concentration of later fractions from the silica gel column described in this procedure and crystallization of the crude residue in methanol afforded an 8% yield of Compound 9: mp, 250°–252° C. (inserted at 110° C., 3° C./min); TLC, 1 spot identical to authentic Compound 9 (40 and 80 mcg) applied 95:5 chloroform-methanol); MS (direct-probe temperature, 260° C.) m/e 464 (M), 387 (M—Ph), 243 ($CPh_3$), 221 (M—$CPh_3$).

EXAMPLE 7

(+)-1-[(1α,3α,4α)-3-Azido-4-(hydroxymethyl)cyclopentyl]-5-methyl-2,4(1H,3H)-pyrimidinedione (Compound 15)

Compound 14 (450 mg, 0.89 mmol) was treated with 80% acetic acid (20 mL) and was purified according to the procedure described for the preparation of Compound 11. The glassy residue obtained by concentrating column fractions that contained product (determined by TLC) crystallized when it was triturated with ethyl acetate: yield of Compound 15, 178 mg (76%); mp, 150°–152° C. (inserted at 100° C., 3° C./min); UVmax 273 nm ($\epsilon$10,300) at pH 1, 273 ($\epsilon$10,400) at pH 7, 271 ($\epsilon$8,000) at pH 13; MS (direct-probe temperature, 20° C.) m/e 266 (M+1), 265 (M), 193, 180, 127 (Thy+2H), 126 (Thy+H); IR (strong and medium-strong bands, 2200-700 $cm^{-1}$ region) 2110 s, 1705 s, 1680 sh, 1665 vs, 1340, 1280, 1265, 1025. Anal. Calculated for $C_{11}H_{15}N_5O_3$: C, 49.80; H, 5.70; N, 26.40. Found: C, 49.50; H, 6.02; N, 26.25.

EXAMPLE 8

(+)-1-[(1α,3α,4α)-3-Amino-4-(hydroxymethyl)cyclopentyl]-5-methyl-2,4(1H,3H)-pyrimidinedione (Compound 16)

Compound 16 was prepared from Compound 15 (125 mg, 0.47 mmol) and purified by the procedure described for the preparation of Compound 8. The residual colorless glass crystallized when it was triturated with ethyl acetate, and the crystalline solid was filtered away, washed with ethyl acetate, and dried in vacuo at 56° C. for 2 hours: yield of white crystals, 90 mg (80%); mp, sinters 162° C., melts 165°-168° C. with mild dec (inserted at 100° C., 3° C./min); TLC, 1 spot (40 or 80 mcg applied, 7:3 2-propanol-1M ammonium acetate as developing solvent); UVmax 272 nm ($\epsilon$10,300) at pH 1, 271 ($\epsilon$10,200) at pH 7, 272 ($\epsilon$8,100) at pH 13; MS (FABMS) m/e 240 (M+1); IR (strong and medium-strong bands, 1800-400 cm$^{-1}$ region) 1680, 1665 sh, 1640 sh, 1605 sh, 1370, 1290, 1075, 760, 585, 425. Anal. Calculated for $C_{11}H_{17}N_3O_3$): C, 55.21; H, 7.16; N, 17.56. Found: C, 55.23; H, 7.26; N, 17.77.

TABLE 1

| | Ultraviolet Absorption Data | | | | | |
|---|---|---|---|---|---|---|
| | 0.1 N HCl[a] | | pH7[b] | | 0.1 N NaOH[a] | |
| Compound | λ max | ε | λ max | ε | λ max | ε |
| 8 | 273 | 10,000 | 273 | 10,400 | 272 | 8,100 |
| 11 | 273 | 10,900 | 273 | 11,000 | 271 | 8,400 |
| 12 | 272 | 10,000 | 273 | 10,300 | 271 | 8,000 |
| 15 | 273 | 10,300 | 273 | 10,400 | 271 | 8,000 |
| 16 | 272 | 10,300 | 271 | 10,200 | 272 | 8,100 |

[a]See paragraph preceding Example 1.
[b]Phosphate buffer.

TABLE 2

Proton NMR Data for Carbocyclic Analogues of 3'-Azido- and 3'-Amino-2',3'-(dideoxypentofuranosyl)thymines.

| Compound | 1 | 2 | 3 | 4 | 5 | CH$_2$O | CH$_3$ | Pyrim. C6 | NH | Other |
|---|---|---|---|---|---|---|---|---|---|---|
| TrOCH$_2$—Th / N$_3$  10 | 4.85 (m, 1H) | 1.96 (m, 1H) 2.16 (m, 3H)$^a$ | 4.08 (m, 1H) | 2.16 (m, 3H)$^a$ | 1.56 (m, 1H) 2.16 (m, 3H)$^a$ | 3.12 (d, 2H) | 1.76 (s, 3H) | 7.54 (s, 1H) | 11.22 (s) | 7.33 (m, 15H, tr) |
| TrOCH$_2$—Th / N$_3$  14 | 4.96 (m, 1H) | 1.71 (m, 1H) 2.50 (m, 2H)$^b$ | 4.39 (m, 1H) | 2.50 (m, 2H)$^b$ | 1.36 (m, 1H) 1.96 (m, 1H) | 3.02 (t, 1H) 3.18 (m, 1H) | 1.73 (s, 3H) | 7.35 (m, 16H)$^c$ | 11.2 (s) | 7.35 (m, 16H, tr)$^e$ |
| HOCH$_2$—Th / N$_3$  11 | 4.84 (m, 2H)$^e$ | 1.91 (m, 1H) 2.10 (m, 3H)$^d$ | 4.06 (m, 1H) | 2.10 (m, 3H)$^d$ | 1.51 (m, 1H) 2.10 (m, 3H)$^d$ | 3.48 (m, 2H) | 1.78 (s, 3H) | 7.57 (s, 1H) | 11.22 (s) | 4.84 (m, 2H, OH)$^e$ |
| HOCH$_2$—Th / N$_3$  15 | 4.93 (m, 1H) | 1.75 (m, 1H) 2.44 (m, 1H) | 4.23 (m, 1H) | 2.20 (m, 2H) | 1.46 (m, 1H) 1.97 (m, 1H) | 3.55 (m, 2H) | 1.80 (s, 3H) | 7.47 (s, 1H) | 11.21 (s) | 4.70 (t, 1H, OH) |
| HOCH$_2$—Th / NH$_2$  12 | 4.96 (m, 1H) | 1.67 (m, 2H)$^f$ 1.90 (m, 1H) | 3.18 (m, 1H) | 1.67 (m, 2H)$^f$ | 1.42 (m, 1H) 2.01 (m, 1H) | 3.48 (m, 2H) | 1.78 (s, 3H) | 7.52 (s, 1H) | | |
| HOCH$_2$—Th / NH$_2$  16 | 4.88 (m, 1H) | 1.39 (m, 1H) 2.24 (m, 1H) | 3.39 (m, 1H) | 1.90 (m, 2H)$^g$ | 1.54 (m, 1H) 1.90 (m, 2H)$^g$ | 3.52 (m, 2H) | 1.78 (s, 3H) | 7.95 (s, 1H) | | |

$^a$Center of overlapping multiplets from protons at positions 2, 4, and 5.
$^b$Center of overlapping multiplets from protons at positions 2 and 4.
$^c$Center of overlapping multiplets from trityl and pyrimidine C6 protons.
$^d$Center of overlapping multiplets from protons at positions 2, 4, and 5.
$^e$Center of overlapping multiplets from protons at position 1 and OH of CH$_2$OH.
$^f$Center of overlapping multiplets from protons at positions 2 and 4.
$^g$Center of overlapping multiplets from protons at positions 4 and 5.

EXAMPLE 9

Antiviral Evaluations In Vitro

The compounds listed in Table 3 were tested for inhibition of the cytopathogenic effects produced by strain 377 (TK+) or strain HF (TK−) of type 1 herpes simplex virus (HSV-1) or strain MS of type 2 herpes simplex virus (HSV-2). The data summarized in Table 3 were acquired by methods and procedures described previously for the evaluation of compounds for antiviral activity in vitro (Shannon et al, *Antimicrob. Agents Chemother.*, 1981, 20, 769–776). The general assay method was described by Ehrlich et al (*Ann. N.Y. Acad. Sci.*, 1965, 130, 5–16), but some modifications were incorporated. The prescription antiviral drug ara-A was employed as a positive control drug in the experiments summarized in Table 3. The data in Table 3 demonstrate that Compounds 8 and 12 are comparable in activity to ara-A in inhibiting replication of HSV-1 in L929 cells.

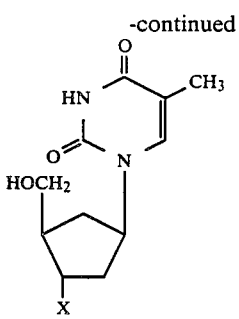

Formula II

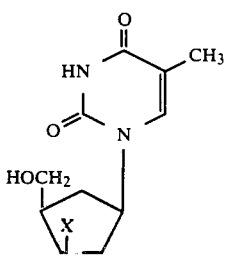

Formula III

TABLE 3
Evaluation of Carbocyclic Analogues of Azido and Amino (Dideoxypentofuranosyl)thymines for Antiviral Activity.[a]

| Compound | HSV-1, Strain 377 | | | | Other Viruses | | | |
|---|---|---|---|---|---|---|---|---|
| | Expt. No.[b] | Host Cells[c] | VR | Ratio VR/VR of ara-A[d] | Expt. No.[b] | Virus[e] | Host Cells[c] | VR |
| C—5'-azido-5'-dThd (7) | 1 | L929 | 0.8 | 0.27 | 1 | HSV-2 MS | L929 | 0 |
| | | | | | 6 | HSV-1 HF | H.Ep.-2 | 0 |
| C—5'-amino-5'-dThd (8) | 1 | L929 | 3.0 | 1 | 1 | HSV-2 MS | L929 | 0.5[f] |
| | 2 | L929 | 1.8 | 1.28 | 6 | HSV-1 HF | H.Ep.-2 | 0.2 |
| | 3 | Vero | 0 | | | | | |
| | 4 | Vero | 0 | | | | | |
| C—3'-azido-3'-dThd (11) | 5 | Vero | 0 | | | | | |
| C—3'-amino-3'-dThd (12) | 2 | L929 | 0.9 | 0.9 | | | | |
| | 2 | Vero | 0 | | | | | |
| | 5 | Vero | 0 | | | | | |
| C—3'-azido-2',3'-dideoxylyxo-Thy (15) | 1 | L929 | 0.2 | | 1 | HSV-2 MS | L929 | 0 |
| | 2 | L929 | 0 | | | | | |
| | 2 | Vero | 0.6 | 0.43 | | | | |
| | 3 | Vero | 1.0 | 0.50 | | | | |
| | 4 | Vero | 0.8 | 0.44 | | | | |
| C—3'-amino-2',3'-dideoxylyxo-Thy (16) | 2 | L929 | 0.4 | 0.4 | | | | |
| | 2 | Vero | 0 | | | | | |
| | 4 | Vero | 0 | | | | | |

[a]The antiviral activity of each compound is expressed as a virus rating (VR). The VR, determined by the general method of Ehrlich et al., supra, is a weighted measurement of antiviral activity that takes into account both the degree of inhibition of virus-induced cytopathogenic effects and the degree of cytotoxicity produced by the test compound. A VR equal to or greater than 1.0 indicates definite and significant antiviral activity, a VR of 0.5–0.9 indicates marginal to moderate antiviral activity, and a VR less than 0.5 usually indicates no significant antiviral activity.
[b]Tests that were performed simultaneously can be identified by Experiment number.
[c]L929 cells are mouse connective tissue cells, clone L. Vero cells are African green monkey kidney cells. H.Ep.-2 cells are human epidermoid carcinoma cells, No. 2.
[d]VR/VR of ara-A is the ratio of the VR of the thymidine analogue to the VR of ara-A (employed as a positive control) in the same experiment.
[e]HSV-2 MS is strain MS (TK+) of type 2 herpes simplex virus. HSV-1 HF is strain HF (TK−) of type 1 herpes simplex virus.
[f]VR/VR of ara-A = 0.36.

What is claimed is:

1. A compound having one of the following formulas:

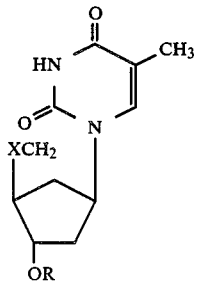

Formula I wherein X is an azido group or an amino group and R is hydrogen or an acyl group having from 2-7 carbon atoms.

2. A compound as defined in claim 1 having Formula I wherein X is an azido group and R is an acetyl group.

3. A compound as defined in claim 1 having Formula I wherein X is an azido group and R is hydrogen.

4. A compound as defined in claim 1 having Formula I wherein X is an amino group and R is hydrogen.

5. (+)-1-[(1α,3β,4α)-3-Azido-4-[(triphenylmethoxy)methyl]cyclopentyl]-5-methyl-2,4-(1H,3H)-pyrimidinedione.

6. A compound as defined in claim 1 having Formula II wherein X is an azido group.

7. A compound as defined in claim 1 having Formula II wherein X is an amino group.

8. (+)-1-[(1α,3α,4α)-3-Azido-4-[(triphenylmethoxy)methyl]cyclopentyl]-5-methyl-2,4(1H,3H)-pyrimidinedione.

9. A compound as defined in claim 1 having Formula III wherein X is an azido group.

10. A compound as defined in claim 1 having Formula III wherein X is an amino group.

11. A process for the treatment of a host animal having a herpes virus infection which comprises administering to said host animal a therapeutically effective amount of a compound as defined in claim 3.

12. A process for the treatment of a host animal having a herpes virus infection which comprises administering to said host animal a therapeutically effective amount of a compound as defined in claim 4.

13. A process for the treatment of a host animal having a herpes virus infection which comprises administering to said host animal a therapeutically effective amount of a compound as defined in claim 7.

14. A process for the treatment of a host animal having a herpes virus infection which comprises administering to said host animal a therapeutically effective amount of a compound as defined in claim 9.

* * * * *